United States Patent [19]

Magdassi et al.

[11] Patent Number: 5,518,736
[45] Date of Patent: May 21, 1996

[54] METHOD OF PREPARING NATURAL-OIL-CONTAINING EMULSIONS AND MICROCAPSULES AND ITS USES

[75] Inventors: Shlomo Magdassi; Kosta Mumcuoglu, both of Jerusalem; Uri Bach, Efrat, all of Israel

[73] Assignee: Yissum Research Development Company of the Hebrew, Jerusalem, Israel

[21] Appl. No.: 266,025

[22] Filed: Jun. 27, 1994

[51] Int. Cl.[6] .............................. A61K 9/50; A61K 9/52; A61K 35/78; A01N 65/00

[52] U.S. Cl. ............ 424/451; 424/195.1; 424/403; 424/405; 424/408; 424/455; 424/457; 424/489; 424/DIG. 10; 514/880; 514/881; 514/937; 514/963; 514/975; 514/919

[58] Field of Search ............................ 424/451, 405, 424/408, 489, 195.1; 514/880, 881

[56] References Cited

U.S. PATENT DOCUMENTS

5,182,105  1/1993  Takata et al. ............... 424/78.02
5,401,502  3/1995  Wunderlich et al. ......... 424/195.1

Primary Examiner—Thurman K. Page
Assistant Examiner—James M. Spear
Attorney, Agent, or Firm—William S. Frommer

[57] ABSTRACT

The invention relates to sustained-release biodegradable lice repelling preparations comprising as active ingredient a lice repelling agent comprising at least one natural oil selected from the group consisting of citronella oil, rosemary oil and eucalyptus oil, or at least one natural oil component selected from the group consisting of citronellal and geraniol or mixtures thereof and further comprising an anionic emulsifier and chitosan, optionally further comprising dermatologically acceptable additives, carriers or diluents. The preparations may be in the form of an aqueous emulsion or chitosan microcapsules, preferably prepared by the processes of the invention.

13 Claims, 5 Drawing Sheets

METHOD OF PREPARING NATURAL-OIL-CONTAINING EMULSIONS AND MICROCAPSULES AND ITS USES

FIELD OF THE INVENTION

The invention relates to a method for the preparation of biodegradable, natural-oil-containing emulsions and microcapsules. The emulsions and microcapsules are particularly useful as active ingredients in lice repelling and other, such as vitamin preparations, which are also encompassed by the invention.

BACKGROUND OF THE INVENTION

Formation of microcapsules, capsules or beads by chitosan was suggested for encapsulation of pharmaceuticals, enzymes, cells, etc. The reported procedures are based on:

A. Using a combination of chitosan, which is a polycationic substance, with a polyanionic substance such as gum Arabic, by a method known as complex coacervation (e.g. JP 87-173464). By this method, an insoluble polymeric shell is produced.

B. Formation of the microcapsules by dispersing an aqueous solution, which contains chitosan, in an oil phase, followed by gelling (e.g. JP 90-317739). This method is based on formation of a separate phase in oil, followed by gellification of the aqueous droplet, and not only the interface.

C. Covalent crosslinking of e.g. beads, by using special cross-linking agents, followed by UV irradiation (e.g. WO 87-US1495).

D. Formation of polymeric spheres by providing droplets of polyanion monomer solution, which meets a stream of polycation monomer solution (e.g. WO (b 92-US9781). This method is based on technology which allows specific contact points between the reactants, and the resulting particle size is controlled by the machinery.

E. Formation of beads, by emulsification of an oil phase directly into a chitosan solution, which is then dropwise added into a solution containing diphosphate and glyoxal hydrate, which leads to crosslinking (e.g. EP 543572). Here, there is no microencapsulation process which occurs at the oil-water interface, but a simple gellification of the whole bead.

As will be shown in the following description, the process of the invention is based on formation of an insoluble wall around each, or only few droplets, in such manner that this wall separates each oil droplet from the aqueous phase.

Formation of biodegradable chitosan-containing aqueous emulsions or sustained release chitosan microcapsules, which have good adhering properties to negatively charged surfaces is desired, and would have a particular advantage for providing natural oil containing biodegradable long-acting lice repelling compositions.

The number of cases of human lice infestation throughout the world is estimated at hundreds of millions each year [Taplin, D. and T. L. Meinking, Sem. Dermatol. (1987) 6:125–135]. The conventional treatment for head lice consists of using synthetic ingredients, which are licidals. However, these chemicals do not solve the problem of reinfestation, which occurs frequently among children. Therefore, the need for a lice repellent is clear.

Insect repellents mostly operate from a distance by confusing the insect's direction finding mechanisms and close up by acting as sensory blockers [Wright, R. H., Sci. Amer. (1975) 233:104–111]. They render the host animal unattractive and in this way protect the host animal from the bites of insects, or ticks and the most pathogenic microorganisms which they transfer. Repellents are normally volatile and consequently remain on the user for a limited period of time.

in the past, lavender oil was used to protect children from head lice infestation [Burgess, I. Br. J. Dermatol. (1993$^a$) 128:357–358]. Recently piperonal (1,3-benzodioxol-5-carboxaldehyde) was introduced as a repellent to the market [Burgess, I. Pharmaceutical J. (1993$^b$) 15:674–675], however, it was shown earlier that this substance has also pediculicidal activity [Moore, W. JAMA (1918) 71:530–531].

The U.S. army has for a long time applied the following repellents to clothing, against body lice: M-1960 (30% 2-butyl-2-ethyl 1–3 propanediol, 30% benzyl benzoate, 30% n-butylacetanilidine and 10% TWEEN 80), 90% benzyl benzoate and a combination of 75% N,N-diethyl-m-toluamide (DEET) and 25% ethanol. Pyrethrum has been used to impregnate underwear, and has both a repellent and toxic effect [Eldridge, B. F., In: The control of lice and louse-borne diseases (1973) PAHO/WHO Sci. Pub. No. 263, pp 177–178].

Today the US and Australian armies are using permethrin and di-butylphthalate as a clothing treatment against a number of medically important arthropods, particularly mosquitoes and chiggers [Gubta, R. K. et al., J. Am. Mosq. Control Assn. (1987) 3: 556–560; Frances, S. P. et al., J. Med. Entomol. (1992) 29:907–910].

The repellent DEET, which is widely used against several arthropods of medical importance, exhibits several side-effects including cardiovascular effects, encephalopathies, allergic and psychotic reactions [Robbins, P. J. and M. G. Cherniak, J. Toxicol, Environ, Health (1986) 18:503; Edwards, D. L. and C. E. Johnson, Clin. Pharm. (1987) 6:496–498; Leach, G. J. et al., J. Toxicol. Environ. Health (1988) 25:217].

It is therefore clear why a natural lice repellent composition is required, especially if formulated in such a way that it would yield long duration of lice repellency.

Sustained release preparations of other oily active agents, such as vitamin E or oil-soluble UV radiation photoprotectants has also encountered problems. For example, the optical properties of photoprotectants are required while they stay on the skin. However, the contact between the skin and the photoprotectant is often a problem, due to the chemical composition of the protectant, which might cause allergenic effects, and is in some cases also cause skin deseases.

SUMMARY OF THE INVENTION

The present invention relates to a process for preparing an aqueous emulsion of an oil comprising the steps of (a) forming an oil-in-water emulsion by homogenizing said oil into an aqueous solution containing an anionic emulsifier; and (b) adding to the emulsion obtained in (a) an aqueous chitosan solution while continuously homogenizing the mixture to give a stable emulsion.

The invention further relates to a process for the microcapsulation of fine oil droplets dispersed in an aqueous solution comprising the steps of (a) forming an oil-in-water emulsion, by homogenizing oil, water and an anionic emulsifier; (b) adding to the emulsion obtained in (a) an aqueous chitosan solution while continuously homogenizing the mixture to give a stable emulsion and optionally diluting this stable emulsion in water or a suitable aqueous solution; (c) adding to the emulsion obtained in (b) a water soluble cross-linking electrolyte which is capable of increasing the pH of the solution and of cross-linking the chitosan polymeric chains, a pH of from about 5 to about 7.5 being maintained by adding a suitable acid, and stirring the mixture for a suitable period of time to give a dispersion of fine microcapsules in water; and (d) optionally removing the aqueous phase from the dispersion obtained in (c) to give a powder.

In the process according to the invention the formation of wall capsule is at the oil-water interface, thus microcapsules, and not beads, are obtained.

In addition, the invention relates to a sustained-release biodegradable lice repelling preparation comprising as active ingredient a lice repelling agent comprising at least one natural oil selected from the group consisting of citronella oil, rosemary oil and eucalyptus oil, or at least one natural oil component selected from the group consisting of citronellal and geraniol or mixtures thereof; an anionic emulsifier; chitosan; and optionally further comprising dermatologically acceptable additives, carriers or diluents.

In particular embodiments the sustained-release biodegradable lice repelling preparations of the invention may be in the form of an aqueous emulsion or the active ingredient may be in the form of chitosan microcapsules.

The particular embodiments of the sustained-release lice repelling preparations of the invention may be prepared by the process of the invention.

Further, the invention relates to sustained release preparations comprising as active ingredient vitamin E or a UV radiation photo-protectant; an anionic emulsifier; chitosan; and optionally further comprising pharmaceutically acceptable additive, carriers or diluents.

DETAILED DESCRIPTION OF THE INVENTION

In a first embodiment, the invention relates to a process for preparing an aqueous emulsion of an oil comprising the steps of (a) forming an oil-in-water emulsion by homogenizing said oil into an aqueous solution containing an anionic emulsifier; and (b) adding to the emulsion obtained in (a) an aqueous chitosan solution while continuously homogenizing the mixture to give a stable emulsion.

In a second embodiment, the invention relates to a process for the microcapsulation of fine oil droplets dispersed in an aqueous solution comprising the steps of (a) forming an oil-in-water emulsion, by homogenizing oil, water and an anionic emulsifier; (b) adding to the emulsion obtained in (a) an aqueous chitosan solution while continuously homogenizing the mixture to give a stable emulsion and optionally diluting this stable emulsion in water or a suitable aqueous solution; (c) adding to the emulsion obtained in (b) a water soluble cross-linking electrolyte which is capable of increasing the pH of the solution and of cross-linking the chitosan polymeric chains, a pH of from about 5 to about 7.5 being maintained by adding a suitable acid, and stirring the mixture for a suitable period of time to give a dispersion of fine microcapsules in water; and (d) optionally removing the aqueous phase from the dispersion obtained in (c) to give a powder.

In the processes of the invention said oil can be a natural oil, a synthetic oil, a natural oil component, soybean oil, vitamin E, oil-soluble UV radiation photoprotectants, D-limonen, a fruit extract or a flavoring extract or a mixture thereof.

For preparing the lice repelling preparations of the invention said oil is a natural oil, preferably rosemary oil, citronella oil, or eucalyptus oil or a mixture thereof, or a natural oil component, preferably citronellal or geraniol or a mixture thereof, or mixtures of these natural oils and natural oil components.

The anionic emulsifier can be sodium dodecyl sulphate, a phospholipid or a mixture of phospholipids such as lecithin, or a soap, such as sodium, potassium or ammonium stearate, oleate or palmitate. Lecithin is a preferred emulsifier.

In the processes of the invention the pH of the chitosan solution employed in step (b) is about 1–2.5 and the final pH of the stable emulsion obtained is about 3.5 the pH can be adjusted by any suitable acid, for example 10% citric acid or 10% acetic.

In the process according to the second embodiment, the cross-linking electrolyte is a water soluble polyphosphate, such as tripolyphosphate, preferably sodium or potassium tripolyphosphate. In step (c) of this process, the acid employed is preferably an organic acid, such as citric, acetic or fumaric acid and said suitable period of time is from 2 to 6 hrs. In step (d) of this process, the aqueous phase can be removed from the dispersion obtained in step (c) by lyophylization, spray-drying or oven vaccum drying at a suitable temperature.

In both embodiments, the process according to the invention may further comprise, after step (b), the addition of a dispersing agent which may be an anionic or cationic surfactant. For example, sodium dodecyl sulphate (SDS) or CTAB may be employed. The addition of the surfactant prevents agglomeration of particles during said step (c).

The invention also relates to sustained-release biodegradable lice repelling preparations comprising, as active ingredient, a lice repelling agent comprising at least one natural oil selected from the group consisting of citronella oil, rosemary oil and eucalyptus oil, or at least one natural oil component selected from the group consisting of citronellal and geraniol or mixtures thereof; an anionic emulsifier; chitosan; and optionally further comprising dermatologically acceptable additives, carriers or diluents.

The sustained-release biodegradable lice repelling preparation may be in the form of an aqueous emulsion of said oil. The anionic emulsifier is a phospholipid or a mixture of phospholipids, lecithin being preferred.

In a preferred embodiment, sustained release biodegradable lice repelling composition according to the invention, in the form of an oil-in-water emulsion, is prepared by the process according to said first embodiment of the invention.

Alternatively, the active ingredient in the lice repelling biodegradable preparation according to the invention may be present in the form of chitosan microcapsules. Preferably, the chitosan microcapsules are prepared by the process according to said second embodiment of the invention.

In both the emulsion form and chitosan microcapsules form, said active lice repelling natural oil is preferably citronella and said active lice repelling natural oil component is geraniol. The lice repelling preparations of the invention may of course contain a mixture of the active natural oil and natural oil components.

The following Examples describe the preparation of oil-in-water emulsion, and of microcapsules in water dispersion for rosemary oil. It is well within the capabilities of the man skilled in the art to use other oils or oil components in a similar manner.

In principle, the process of the invention is based on the following steps:

Formation of oil-in-water emulsion, by using an anionic emulsifier such as, e.g., lecithin; and Addition of chitosan solution of low pH to the above emulsion, while continuously homogenizing. In this step, a stable emulsion, preferably at pH=3.5 is obtained.

The emulsion obtained may then be diluted in distilled water.

In the process for preparing chitosan microcapsules the thus obtained stable emulsion, which preferably has been diluted, is subjected to the following:

Dropwise addition of sodium tripolyphosphate solution into the above diluted emulsion, while the pH is kept constant at 5.3. In this step a dispersion of fine microcapsules in water is obtained.

At the end of the process a dispersion of microcapsules in water is obtained. It is possible to obtain microcapsules powder, simply by lyophilization or drying in fluidized bed of the above dispersion.

In the above process/es an emulsion is formed by an emulsifier, which is capable of interacting with chitosan. In prior art processes employing chitosan, e.g. EP-A-543572, core material is added into the hardening agent solution. This difference allows formation of fine microcapsules, compared to large beads, which are obtained by the other processes. Needless to say, large beads would not be suitable for the purposes of the preparations of the invention.

The lice repelling preparations of the invention can be applied to the hair as such or they can be admixed with hair shampoos or conditioning preparations.

Figure 5:
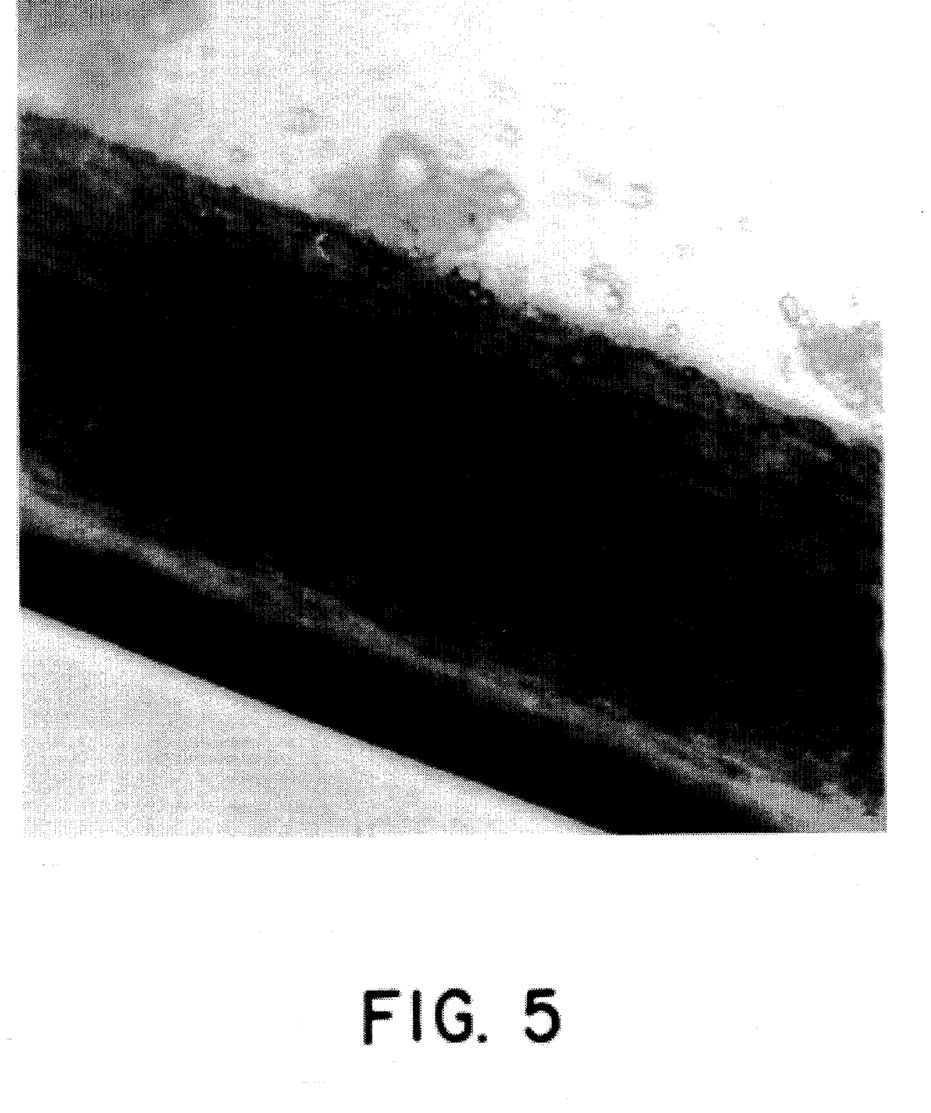
FIG. 5 shows the adhesion of chitosan coated emulsion droplets (microcapsules) onto hair fibers (magnification× 400).

One of the remarkable properties of the chitosan-containing oil-in-water emulsions and the chitosan microcapsules of the invention is the ability of the droplets, in the emulsion, or the microcapsules to adhere onto hair fibers, which are generally negatively charged. This adherance is demonstrated in FIG. 5.

This property is of great significance to the present invention, since the active lice repelling oils or oil components will adhere to the hair, and thereafter will be slowly released, leading to a biodegradable sustained release formulation.

The chitosan microcapsules containing lice repelling preparations of the invention can also be adhered to suitable carrying means, such as decorative tapes, hairpins or earrings, to be worn by the user.

In yet another embodiment, the invention relates to sustained release preparations comprising as active ingredient vitamin E or a UV radiation photoprotectant; an anionic emulsifier; chitosan; and optionally further comprising pharmaceutically acceptable additive, carriers or diluents.

The vitamin E may be in any biologically compatible form of α-tocopherol, or mixtures of different compatible forms.

UV radiation photoprotectants may be, for example, octylmethoxy cinnamate.

In these preparations the active ingredient may be present in the form of an aqueous emulsion, which is preferably prepared by said first embodiment of the process of the invention, or in the form of chitosan microcapsules, preferably prepared by said second embodiment of the process of the invention.

EXAMPLES

Material and Methods

Lice - The human body louse, pediculus humanus humanus, was reared by feeding the lice every 48 hrs on rabbits. Lice were placed on the shaved abdomen of white New Zealand rabbits and left until fed to satiety. Outside the host, the lice were maintained at a temperature of 30° C. and relative humidity of 70–80%. For each test, 20 female lice, which had been fed 24 hrs before, were used.

Chemicals - The natural oils citronella, rosemary, eucalyptus, lavender and D-limonen and essential oils components such as citronellal, geraniol, linalool, bornyl acetate, camphor, cineol, pinene, camphene and borneol were used. Absolute ethanol served as negative control and DEET as positive control.

Bioassay - The petri-dish method was used to examine the repellency of the oil, oil components and control solutions employed. Whatman 4 filter paper discs (5.5 cm in diameter) were placed on petri-dishes. A 100 ml drop of the test solution was placed on a corduroy patch (1.5 cm$^2$). The material was allowed to dry in an incubator at 35° C. and 85–90% relative humidity. Control patches were treated in the same manner. The patches were placed at the periphery of the filter paper at a maximum distance apart from each other. Twenty female lice were placed in the middle of the filter paper and the petri-dish together with the lice were covered with a dark box in order to avoid any influence of light. The number of lice found on the treated and control patches, as well as on the area between the patches, were recorded after 10 min. Each component was tested three times. The duration of repellency was examined by testing the treated patches every 3–4 days. The concentration at which a given substance was still active was examined by preparing serial dilutions and examining the effect one day after treatment of the patches.

Calculations - The repellency was calculated according to the following equation:

$$\% \text{ Repellency} = [(1/2A - n)/1/2A] \times 100$$

where

A=total number of lice n=number of lice found in the treated patch

According to this equation, when lice were evenly distributed between the treated and untreated patches (n=1/2A), % repellency is equal to zero, and when no lice are left in the treated patch (n=0), the repellency is 100%.

Lice Repellency of Natural Oils and Natural Oil Components

Using the above evaluation methods, 14 oils and oil components were tested. The various oil components were tested in their crude form, without purification or special formulation. Results are summarized in Table 1. As shown in Table 1, out of 14 oils and oil components only five samples gave long repellent activity (above 1 week). These are citronella oil, rosemary oil and eucalyptus oil, and the specific active oil components are geraniol and citronellal.

TABLE 1

The Duration of Repellent Activity of
Natural Oils and their Ingredients

| Compound | Activity in days |
| --- | --- |
| citronella | >29 |
| rosemary | >18 |
| eucalyptus | >8 |
| lavender | >1 |
| D-limonen | <1 |
| citronellal | >15 |
| geraniol | >8 |
| linalool | >1 |
| linalool | >1 |
| bornyl acetat | >1 |
| camphor | >1 |
| cineol | <1 |
| pinene | <1 |
| camphene | <1 |
| borneol | <1 |
| citronella emulsion | <8 |
| rosemarry emulsion | >8 |

Figure 1:
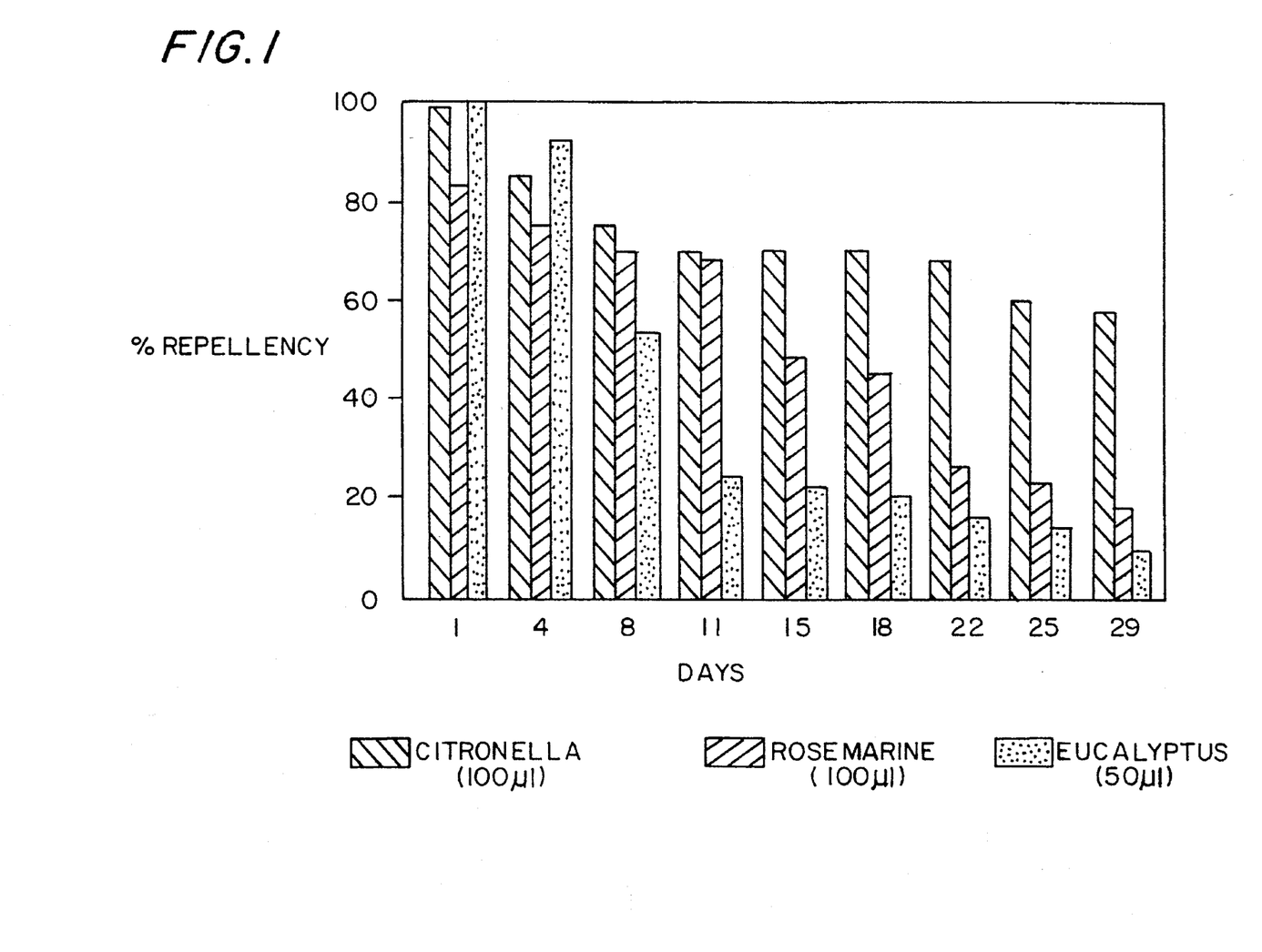
FIG. 1 illustrates the lice repellent effect of citronella, rosemary and eucalyptus oils.

The duration of the repellent activity is demonstrated in FIG. 1, in which the repellency test results are presented at various time intervals. It can be clearly seen that up to 11 days the rosemary and citronella oils have very high and similar activities, while the rosemary oil continues to be effective for as long as one month.

Figure 2:
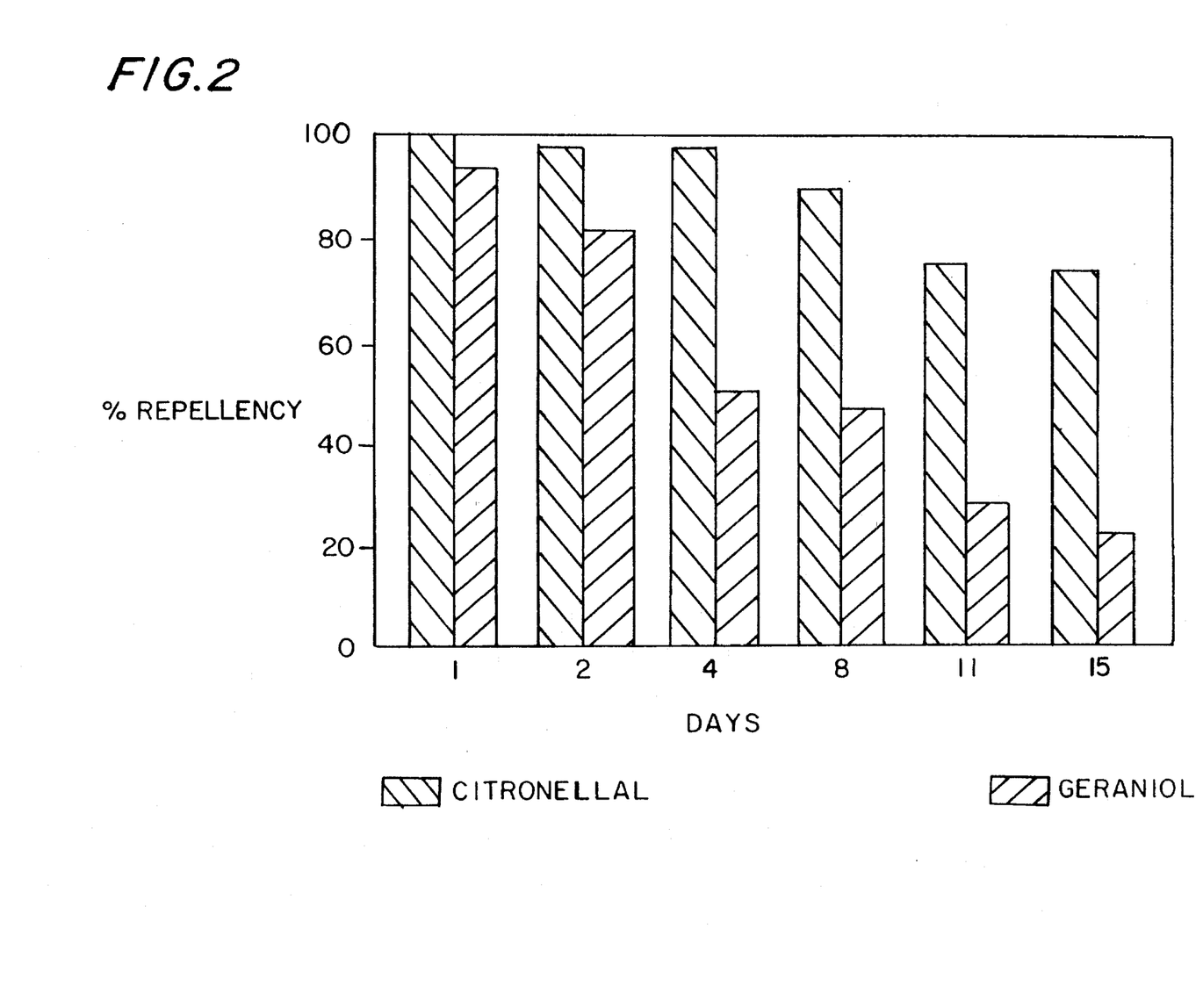
FIG. 2 illustrates the lice repellent effect of citronellal and geraniol.

A similar test was conducted for the individual oil components. As shown in FIG. 2, both citronellal and geraniol have the ability to repel lice, while citronellal has a longer activity duration.

Figure 3:
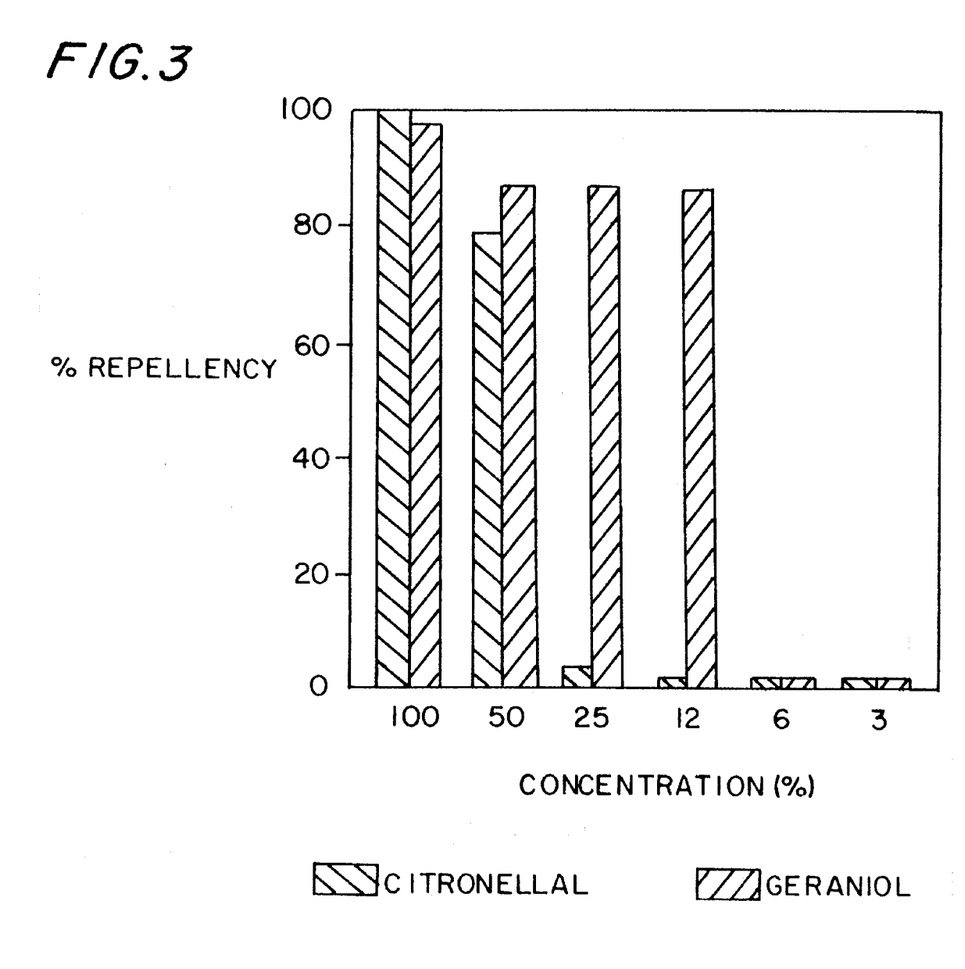
FIG. 3 illustrates the lice repellent effectiveness of various doses of geraniol and citronellal (expressed as % pure component)

These results show that the specific ingredients and three oils can be effective lice repellents. Although the duration of citronellal is longer than that of geraniol, geraniol is still effective at concentrations as low as 12% of the original dose, as shown in FIG. 3.

Lice Repellency of Natural Oils and Natural Oil Components in Aqueous Emulsions

Using the same procedure, the repellency of oil-in-water emulsions, which contained 30% w/w rosemary oil or citronella oil was tested. (The detailed description of emulsion formulation is given hereunder).

Figure 4:
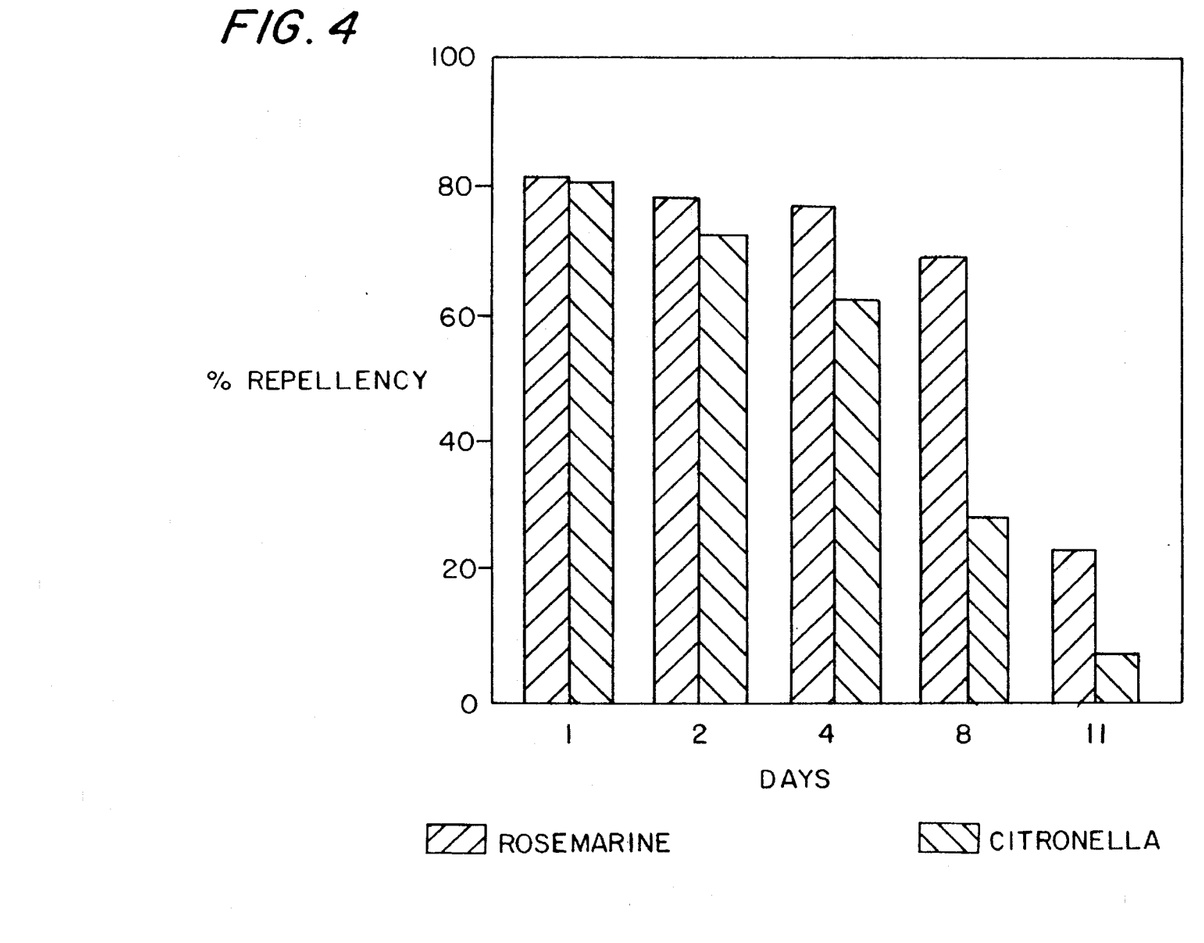
FIG. 4 illustrates the lice repellent effect of rosemary or citronella oil-in-water emulsions prepared with lecithin and chitosan.

A shown in FIG. 4, both emulsions have a long lasting activity; more than 60% repellency, after 4 days for both oils, and 8 days for the rosemary oil in water emulsion. It is obvious that these emulsions can be easily applied directly to the hair, either in liquid form or by spraying on the hair.

Preparation of Emulsion

30% w/w rosemary oil were dropwise added into a 1% w/w lecithin (centrolex P®) solution in water, while continuously homogenizing the system by a homogenizer. The lecithin solution was brought to pH=4.5 by citric acid, prior to addition of the oil phase. The homogenization was continued for 20 min, after which a white emulsion with an average droplet diameter of 2 μm was obtained while the droplets were negatively charged. A 2% w/w chitosan solution was separately prepared by dissolving chitosan into a 10% w/w citric acid solution. During the next step, the chitosan solution was dropwise added to the emulsion, while homogenizing, for 20 min. The volume of the added chitosan solution was half the volume of the emulsion.

The final composition of the emulsion was:

| rosemary oil | 15% w/w |
| --- | --- |
| chitosan | 0.5% w/w |
| citric acid | 5% w/w |
| lecithin | 0.35% w/w |
| $H_2O$ | 79.15% w/w |

The final pH of the emulsion was 3.5. This emulsion is stable for at least 8 months at room temperature.

Using this formulation, the lice repellency of two emulsions was tested: rosemary oil and citronella oil. It was found that both emulsions had a lice repelling activity, as shown in FIG. 3. Since only 15% of the emulsion sample is the oil phase, the repellency results are very impressive: only 15 μl of the oil (compared to 100 μl, FIG. 1) are capable of repelling lice for about one week. These results demonstrate the unique property of these emulsions, which is the slow release of the active ingredients.

Adhesion to Hair Fibers

Chitosan microcapsules containing rosemary oil were applied to human hair fibers by dipping the hair into the dispersion. As demonstrated in FIG. 5, the microcapsules adhered to the hair fiber. Therefore, it is expected that the rosemary oil will be slowly released at the vicinity of the hair fiber, repelling the lice.

Microencapsulation

The microencapsulation process is based on formation of an insoluble layer of chitosan, around the emulsion droplets. The following is a representative example.

1. 20 ml of the above emulsion are mixed with 50 ml distilled water, while stirring at low speed.

2. 100 ml of sodium tripolyphosphate (STPP) solution (4% w/w) are added dropwise to the above diluted emulsion, with continuous stirring at low speed for about 4 hrs. The pH is maintained constant at 5.3, with the aid of suitable addition of citric acid solution.

At the end of the process a dispersion of microcapsules in water is obtained. It is possible to obtain microcapsules powder, simply by lyophilization or drying in fluidized bed of the above dispersion.

Preparation of Vitamin E Microcapsules

A 1% lecithine (centrolex®, which is stored under freezing) was prepared by dissolution in water. After the licithine is dissolved, the pH of the solution is adjusted to pH 4.5 by adding citric acid.

A 30% emulsion of vitamin E is prepared by adding the oily vitamin into the lecithine solution, while constantly homogenizing for about 20 min. until a yellow homogenous emulsion is obtained.

A 2% (w/w) chitosan solution is prepared by introducing the required quantity of chitosan into 10% citric acid. The mixture is stirred for about 2 hrs and filtered through a stainless steel sieve to remove contaminations which were present in the chitosan.

The chitosan solution is then slowly added into the vitamin E emulsion at a 1:1 ratio, while constantly homogenizing for about 30 min.

The microcapsules are solidified by adding a 5% NaOH solution to the above emulsion until a pH of about 6 is obtained. At this stage the microcapsules float and can be easily filtered off and dried. Final drying is preformed by lyophiliazing for 24 hrs.

We claim:

1. A sustained-release biodegradable lice repelling preparation comprising, in the form of an aqueous emulsion:

(a) as active ingredient a lice repelling agent comprising at least one natural oil selected from the group consisting of citronella oil, rosemary oil and eucalyptus oil, or at least one natural oil component selected from the group consisting of citronellal and geraniol or mixtures thereof;

(b) an anionic emulsifier; and (c) chitosan.

2. A lice repelling biodegradable preparation comprising:

(a) as active ingredient a lice repelling agent comprising at least one natural oil selected from the group consisting of citronella oil, rosemary oil and eucalyptus oil, or at least one natural oil component selected from the group consisting of citronellal and geraniol or mixtures thereof;

(b) an anionic emulsifier; and (c) chitosan, wherein said active ingredient is present in the form of chitosan microcapsules.

3. A sustained-release biodegradable lice repelling preparation according to claim 1 or 2 wherein said anionic emulsifier is a phospholipid or a mixture of phospholipids.

4. A sustained-release biodegradable lice repelling preparation according to claim 2 wherein said anionic emulsifier is lecithin.

5. A sustained release biodegradable lice repelling composition according to claim 1 wherein said emulsion is prepared by the steps of:

(a) forming an oil-in-water emulsion by homogenizing said oil into an aqueous solution containing an anionic emulsifier; and (b) adding to the emulsion obtained in (a) an aqueous chitosan solution while continuously homogenizing the mixture to give a stable emulsion.

6. A lice repelling biodegradable preparation according to claim 2 wherein said active ingredient is present in the form of chitosan microcapsules prepared by the steps of:

(a) forming an oil-in-water emulsion, by homogenizing oil, water and an anionic emulsifier;

(b) adding to the emulsion obtained in (a) an aqueous chitosan solution while continuously homogenizing the mixture to give a stable emulsion and optionally diluting this stable emulsion in water or a suitable aqueous solution; and (c) adding to the emulsion obtained in (b) a water soluble cross-linking electrolyte which is capable of increasing the pH of the solution and of cross-linking the chitosan polymeric chains, a pH of from about 5 to about 7.5 being maintained by adding a suitable acid, and stirring the mixture for a suitable period of time to give a dispersion of fine microcapsules in water.

7. A lice repelling biodegradable preparation according to claim 1 or 2 wherein said natural oil is citronella.

8. A lice repelling biodegradable preparation according to claim 1 or 2 wherein said natural oil component is geraniol.

9. A hair shampoo or conditioning preparation containing a lice repelling composition according to claim 1 or 2.

10. A lice repelling preparation according to claim 2 in which said microcapsules are adhered to suitable carrying means such as decorative tapes, hairpins or earrings.

11. A sustained-release biodegradable lice repelling preparation according to claim 1, which further comprises dermatologically acceptable additives, carriers or diluents.

12. A lice repelling biodegradable preparation according to claim 2, which further comprises dermatologically acceptable additives, carriers or diluents.

13. A lice repelling biodegradable preparation according to claim 6, wherein the steps further comprise removing the aqueous phase from the dispersion obtained in step (c) to give a powder.

* * * * *